United States Patent
Cornelius

[11] Patent Number: 5,571,212
[45] Date of Patent: Nov. 5, 1996

[54] PROSTHETIC ANKLE JOINT FOR PIVOTALLY CONNECTING A RESIDUAL LIMB TO A PROSTHETIC FOOT

[75] Inventor: Craig J. Cornelius, Woodinville, Wash.

[73] Assignee: M+IND (Model & Instrument Development Corporation, Poulsbo, Wash.

[21] Appl. No.: 371,024

[22] Filed: Jan. 10, 1995

[51] Int. Cl.⁶ .................................................. A61F 2/60
[52] U.S. Cl. ............................. 623/48; 623/47; 623/49; 623/52
[58] Field of Search ............................. 623/52, 47, 48, 623/49, 50, 51

[56] References Cited

U.S. PATENT DOCUMENTS

| | | | |
|---|---|---|---|
| 963,796 | 7/1910 | Mueller | 623/52 |
| 1,215,268 | 2/1917 | Hagey | 623/52 |
| 1,779,765 | 10/1930 | Eichhorn | 623/52 |
| 2,605,475 | 8/1952 | Burger et al. | 623/49 |
| 3,196,463 | 7/1965 | Farneth . | |
| 3,754,286 | 8/1973 | Ryan . | |
| 3,851,337 | 12/1974 | Prahl . | |
| 3,982,278 | 9/1976 | May | 623/47 |
| 3,982,280 | 9/1976 | Asbelle et al. . | |
| 4,360,931 | 11/1982 | Hampton . | |
| 4,605,417 | 8/1986 | Fleischauer | 623/49 |
| 4,645,508 | 2/1987 | Shorter et al. | 623/48 |
| 4,718,913 | 1/1988 | Voisin | 623/49 |
| 4,764,172 | 8/1988 | McCoy | 623/49 |
| 5,019,109 | 5/1991 | Voisin | 623/49 |
| 5,112,356 | 5/1992 | Harris et al. | 623/52 |
| 5,158,570 | 10/1992 | Schey et al. | 623/52 |
| 5,258,038 | 11/1993 | Robinson et al. | 623/49 |
| 5,314,499 | 5/1994 | Collier, Jr. | 623/47 |
| 5,443,527 | 8/1995 | Wilson | 623/52 |

FOREIGN PATENT DOCUMENTS

| | | | |
|---|---|---|---|
| 2070439 | 9/1981 | United Kingdom | 623/47 |
| 9217135 | 10/1992 | WIPO | 623/48 |

*Primary Examiner*—John G. Weiss
*Assistant Examiner*—Bruce E. Snow
*Attorney, Agent, or Firm*—Seed and Berry LLP

[57] ABSTRACT

A prosthetic ankle joint includes a first joint structure having a foot attachment plate connecting a pair of spaced apart parallel fins lying in a sagital plane. A second joint structure having a pylon attachment plate is connected to a support block positioned between the fins of the first joint structure. The first and second joint structures are connected to each other by a spherical bearing that allows the joint structures to pivot with respect to each other about three orthogonal axes. The spherical bearing is connected to the first joint structure through an axle that extends through an aperture in the bearing. A rod extending from the bearing is threaded into a bore formed in the support block of the second joint structure. Dorsiflexion and plantar flexion cushions are positioned between the support block and respective surfaces of the first joint structure to resist pivotal dorsiflexal and plantar flexal pivotal movement of the ankle joint. Lateral cushions are positioned on opposite surfaces of the support block between the support block and respective fins to resist coronal and transverse pivotal movements of the ankle joint.

23 Claims, 6 Drawing Sheets

PROSTHETIC ANKLE JOINT FOR PIVOTALLY CONNECTING A RESIDUAL LIMB TO A PROSTHETIC FOOT

TECHNICAL FIELD

The present invention relates to a prosthetic ankle joint, and more particularly, to a prosthetic ankle joint having flexion characteristics that vary as a function of the flexure position of the ankle joint.

BACKGROUND OF THE INVENTION

Individuals who lose all or part of a leg have a residual limb to which a prosthetic foot is often attached through an elongated pylon. The attachment between the lower end of the pylon and the prosthetic foot approximates an ankle joint. However, in the past, pylons have been rigidly attached to prosthetic feet, thus creating a rigid ankle joint. Rigid ankle joints have typically relied on a cushion in the heel of the prosthetic foot to allow relative axial motion between the residual limb and the ground. However, this approach has proven to be inadequate because it makes the individual walk awkwardly, and prone to stumble when standing on an incline.

The basic problem with a rigid ankle joint is that it does not mimic a real ankle. As a result, prosthetic designers have developed pivotal ankle joints. Such ankle joints typically provide some motion in three orthogonal planes, namely the sagital, coronal, and transverse planes. A transverse plane is orthogonal to the longitudinal axis of the residual limb, and movement in the transverse plane is known as transverse adduction or abduction of the foot, or transverse rotation. A sagital plane is a vertical front-to-back plane, and movement in the sagital plane is known as either dorsiflexion in which the toe pivots upwardly or plantar flexion in which the toe pivots downwardly. The coronal plane is a vertical plane orthogonal to the transverse, and rotation in the coronal plane is coronal rotation, i.e., inversion or eversion of the foot.

Some of these pivotal ankles allow for these motions by attaching the residual limb to the prosthetic foot with a resilient material. The resilient material allows the residual limb to move relative to the prosthetic foot in any direction. One problem with such ankles is that they do not allow the resistance of the ankle to dorsiflexion and plantar flexion to be independently adjusted. It is known that it is desirable for the ankle to have greater resistance to dorsiflexion than to plantar flexion so the individual using it will have a natural walking gait. Thus, these ankles are inadequate because they make the individual walk awkwardly.

Some other pivotal ankles do allow independent adjustment of the resistance to plantar flexion and dorsiflexion. An example of such an ankle is U.S. Pat. No. 4,645,508, to Shorter et al. This ankle has a residual limb mounted vertically on a ball and socket joint having an outer sleeve which skirts the front and both sides of the shank of the ball. A ring of resilient material surrounds the shank of the ball and is fitted underneath the sleeve. During dorsiflexion the sleeve restricts expansion of the resilient material as it is compressed by the socket, thus providing resistance to dorsiflexion. During plantar flexion the resilient material is free to expand while it is compressed by the socket, thus providing less resistance to plantar flexion. One problem with this ankle is that because it uses the same ring for dorsiflexion and plantar flexion, it can only provide gross adjustments in resistance. For the individual to have a natural walking gait, fine adjustments are necessary.

Other pivotal ankles can provide finer adjustments by using different resilient materials for dorsiflexion and plantar flexion. An example of such an ankle is U.S. Pat. No. 3,851,337, to Prahl. The ankle disclosed in the Prahl patent has a shaft extending along the longitudinal axis of a residual limb which terminates in an eye socket. The eye socket is pressed onto a spherical bearing which is fitted on an axle mounted in a prosthetic foot. A second spherical bearing is fitted about the shaft of the residual limb, and a second eye socket is pressed onto the second bearing and is connected to a shaft extending toward the toe of the prosthetic foot. The shaft fits through a third spherical bearing and extends into a cylinder. Inside the cylinder both dorsiflexion and plantar flexion are independently resisted by separate cushions of resilient material. By adjusting the resilience of these two cushions, resistance to plantar flexion and dorsiflexion can be independently controlled. However, this ankle requires a complex linkage of sockets and bearings in order to do this while keeping the residual limb mounted vertically over the joint.

Therefore, there is a need in the art for a prosthetic ankle joint of simple construction which provides greater resistance to dorsiflexion than to plantar flexion.

One object of this invention is to allow an individual who has a residual limb to have a stable and natural walking gait.

Another object is to provide a prosthetic ankle joint which, like a natural ankle, allows dorsiflexion, plantar flexion, coronal rotation, and transverse rotation.

A further object is to provide a prosthetic ankle joint of simple construction.

Still another object is to provide a prosthetic ankle joint which is reliable.

A still further object is to provide a prosthetic ankle joint with greater resistance to dorsiflexion than to plantar flexion.

Additional objects, advantages and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

SUMMARY OF THE INVENTION

The inventive prosthetic ankle joint includes first and second joint structures connected to each other by a spherical bearing. The joint structures include respective attachment members that allow the joint structures to be secured between a pylon and a prosthetic foot. The first joint structure preferably includes first and second spaced apart fins each of which substantially lie in a sagital plane. A lateral restraining member attached to the second joint structure has a lateral restraining member positioned between the first and second fins. The spherical bearing pivotally interconnects the joint structures so that they pivot with respect to each about three orthogonal axes. A dorsiflexion cushion is positioned between the first and second joint structures at a location causing the dorsiflexion cushion to be compressed during dorsiflexal pivotal movement of the ankle joint. Similarly, a plantar flexion cushion is positioned between the first and second joint structures at a location causing the plantar flexion cushion to be compressed during plantar flexal pivotal movement of the ankle joint. A stop cushion may also be positioned between the first and second joint structures at a location causing the stop cushion to be compressed during one of either dorsiflexal pivotal movement or plantar flexal pivotal movement of the ankle joint and acting in parallel with the primary cushion. The stop cushion is thinner and made of a stiffer material than the primary cushion. As a result, the torsional spring constant of the prosthetic ankle is greater as the stop cushion is compressed. A lateral cushion is positioned between the lateral restraining member and each of the first and second fins so that the lateral cushions are compressed during coronalflexal and transversflexal pivotal movement of the ankle joint in opposite directions. The pivot point of the spherical bearing is preferably offset from the location where the user's weight is applied to the ankle joint so that the user is supported by both a cushion and the spherical bearing. As a result, the cushion not only provides resistance to dorsiflexion or plantar flexion, but it also cushions the downward force exerted on the ankle by the weight of the user. One of the joint structures may also include a plate lying in a transverse plane having a v-shaped notch extending inwardly from a transverse rear edge of the plate. A restraining member projecting into the notch from the other joint structure causes the restraining member to move into a narrower portion of the notch during plantar flexal movement to progressively stabilize the ankle joint in the coronal plane as the ankle joint pivots in plantar flexion. The dorsiflexion cushion is preferably spaced from the pivot axis of the bearing by a distance that is different than the spacing between the plantar flexion cushion and the bearing. As a result, the torsional spring constant of the prosthetic ankle in dorsiflexion may be different from the torsional spring constant of the prosthetic ankle in plantar flexion using the stone material for the dorsiflexion and plantar flexion cushions.

BRIEF DESCRIPTION OF THE DRAWINGS

These and other features of the present invention will become better understood with regard to the following description, appended claims, and accompanying drawings where:

DETAILED DESCRIPTION OF THE INVENTION

Figure 1:
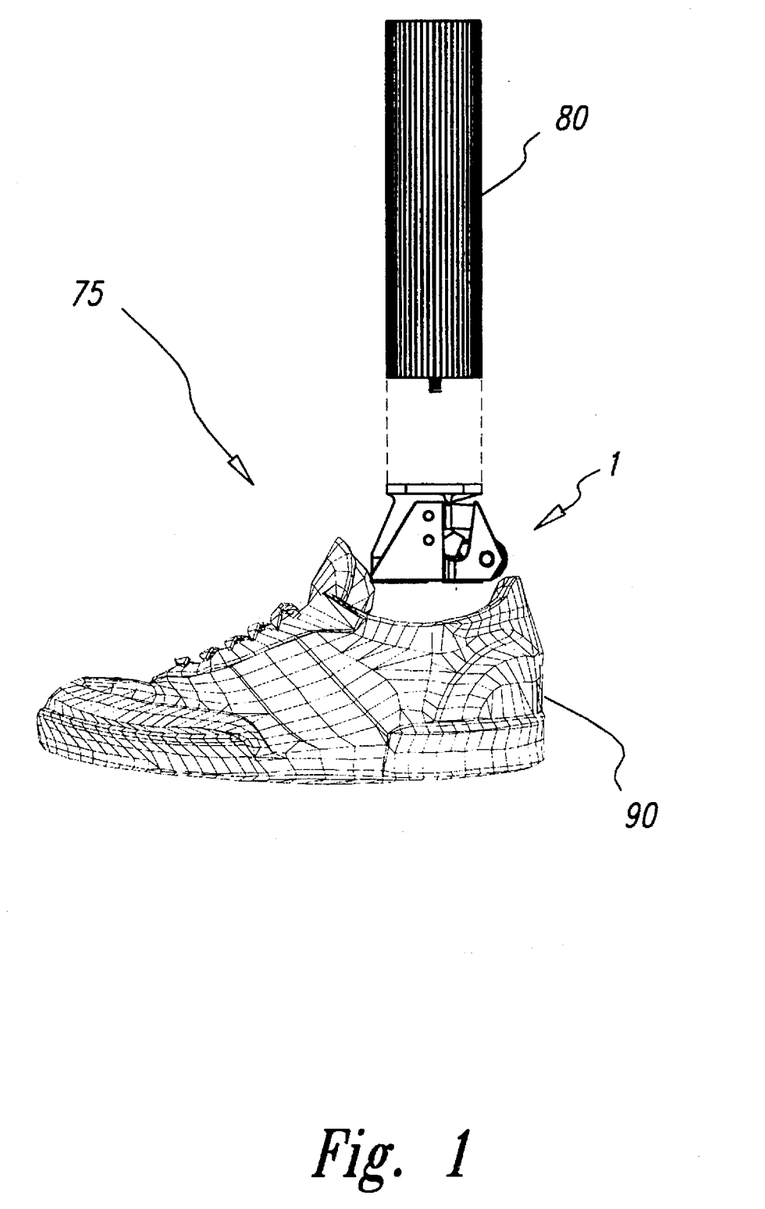
FIG. 1 is a side elevational view of a walking system using the inventive prosthetic ankle joint.

A prosthetic ankle joint 1 is shown in use in FIG. 1 attached to the lower end of a prosthetic pylon 80 and attached to prosthetic foot 90. The prosthetic ankle joint is used by individuals who have lost all or part of a leg to connect a residual limb to a prosthetic foot. The prosthetic ankle joint 1 is intended to mimic as much as possible the motion of a natural ankle by giving an individual who has a residual limb a steady and natural gait. This is because it allows the natural motions of dorsiflexion, plantar flexion, coronal rotation, and transverse rotation. The prosthetic ankle joint is also reliable and relatively inexpensive due to its relatively simple construction. Further, the prosthetic ankle joint provides resistance to plantar flexion and dorsiflexion that is independently adjustable. Finally, the prosthetic ankle joint provides resistance to coronal rotation that is independently adjustable.

Figure 2:
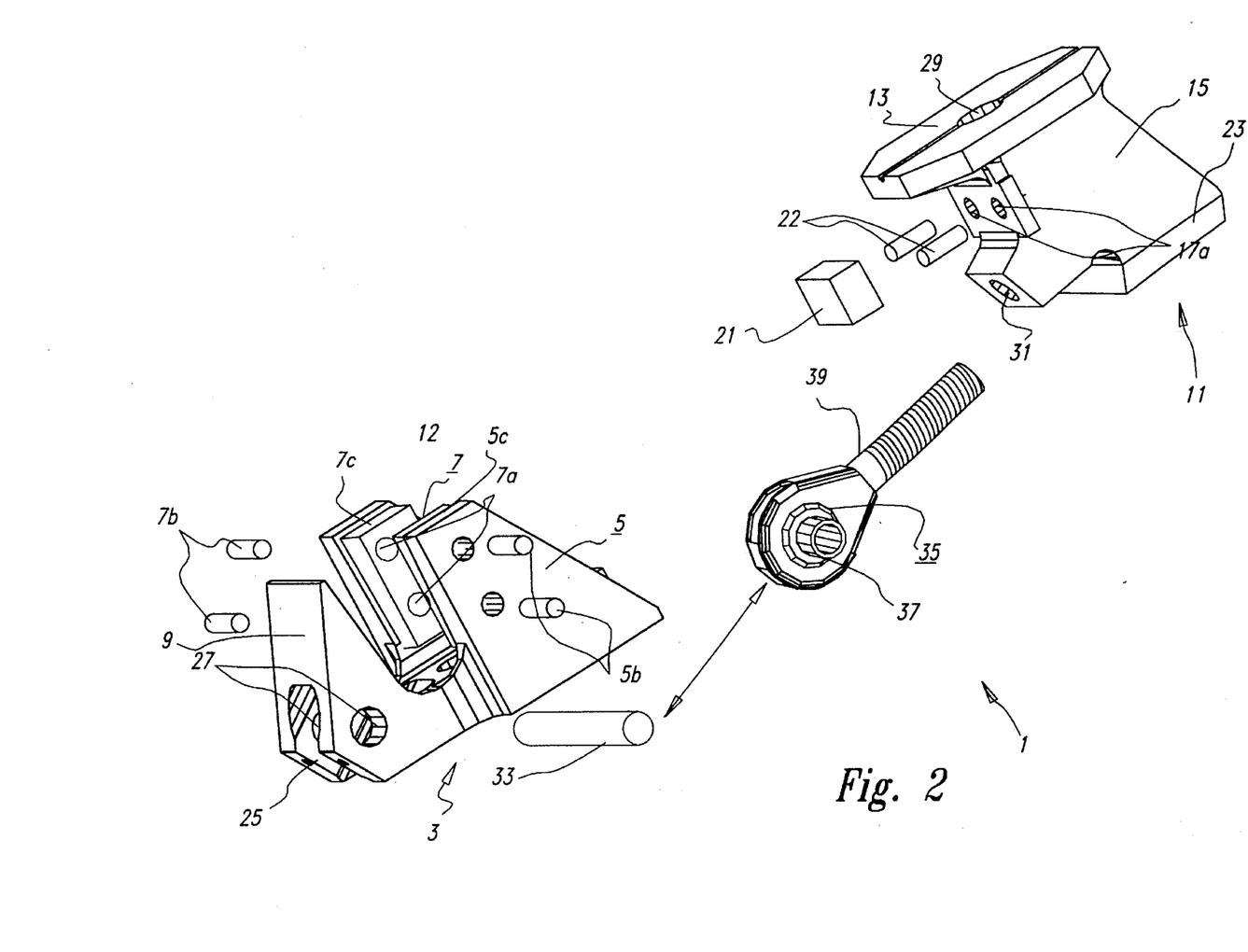
FIG. 2 is an exploded isometric view of a preferred embodiment of the inventive prosthetic ankle joint.

The preceding advantages are provided using the inventive ankle joint 1, one embodiment of which is illustrated in FIG. 2. The prosthetic ankle joint 1 includes a foot attachment structure 3 having a pair of restraining fins 5, 7 and a support block 9. Respective cushions 5c, 7c are mounted on the inner faces of the restraining fins 5, 7 by respective pins 5b, 7b for reasons that are explained in greater detail below.

The prosthetic ankle joint 1 also includes a pylon attachment structure 11 having a pylon attachment plate 13 mounted on a base 15. A pair of cushions 21, 23 are secured to the base 15 to control the flexion characteristics of the ankle joint, as explained in greater detail below. The cushions 21, 23 are secured to the base 15 by respective pairs of pins of which the pins 22 for the cushion 21 are shown in FIG. 2. The pins 22 fit into respective bores 17 formed in base 15.

The pylon attachment structure 11 is mounted in the foot attachment structure 3 between the restraining fins by a spherical bearing 35. A threaded stud 39 projects from the bearing 35 and is threaded in a threaded bore 31 formed in the base 15 of the pylon attachment structure 11. A cylindrical bore 37 formed in the bearing 35 slidably receives a pin 33 that is fixedly inserted through a pair of bores 27 formed in the support block 9 of the foot attachment structure 3. The slidable mounting of the bearing 35 on the pin 33, coupled with the characteristic movement of the spherical bearing 35, allows the pylon attachment structure 11 to rotate about 3 axes while it is maintained in position between the retaining fins 5, 7.

Figure 3:
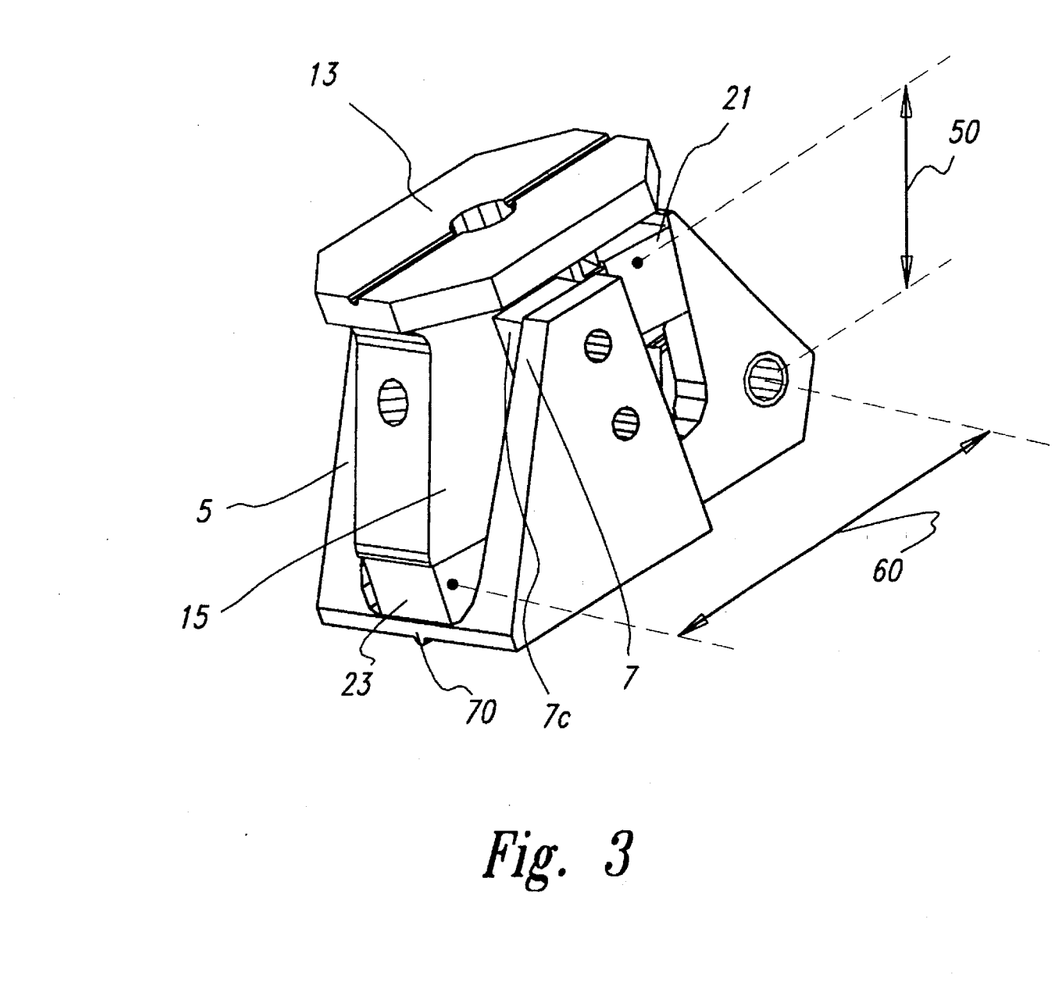
FIG. 3 is an isometric view of the prosthetic ankle joint of FIG. 1 shown in assembled configuration.
Figure 4A:
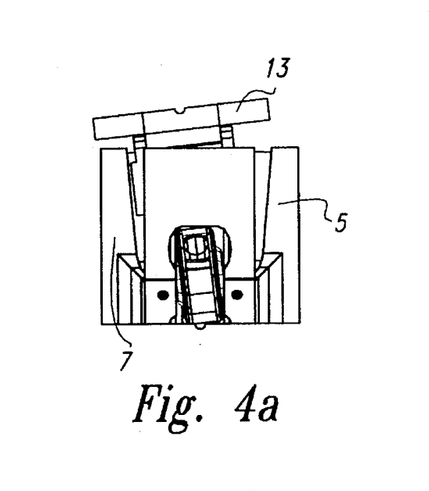
FIGS. 4(a) and (b) are rear elevational views of the prosthetic ankle joint of FIG. 1 showing how the ankle joint accommodates coronal rotation.
Figure 4B:
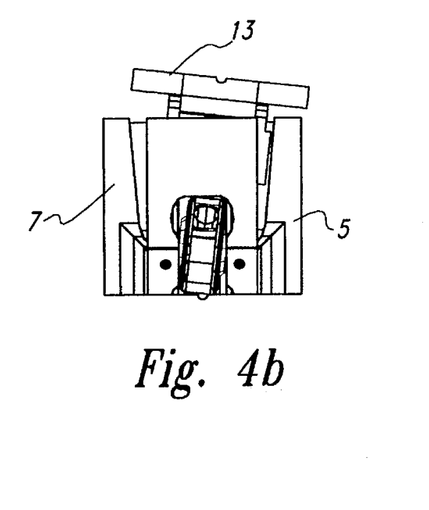
Figure 4C:
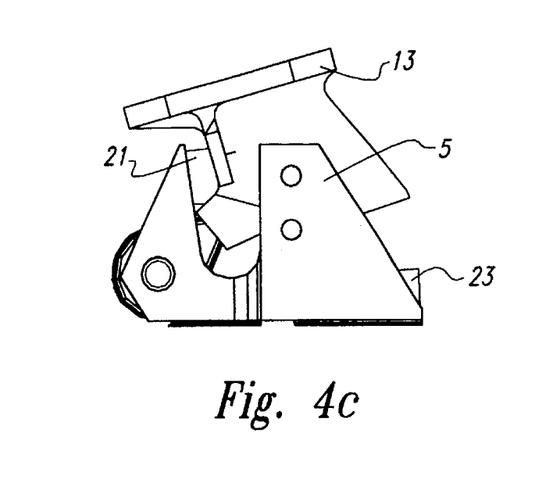
FIGS. 4(c) and (d) are side elevational views of the prosthetic ankle joint of FIG. 1 showing plantar flexion and dorsiflexion.
Figure 4D:
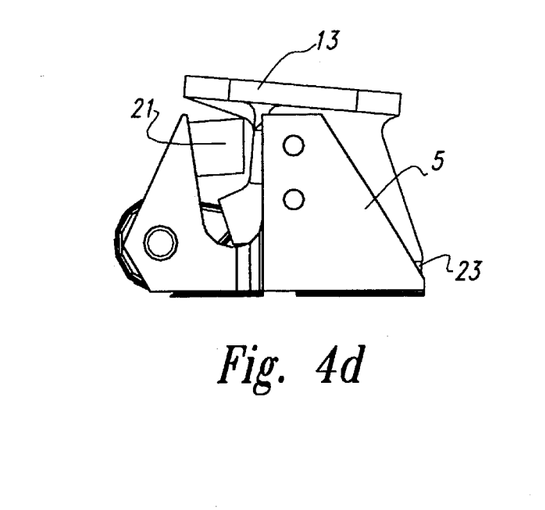
Figure 4E:
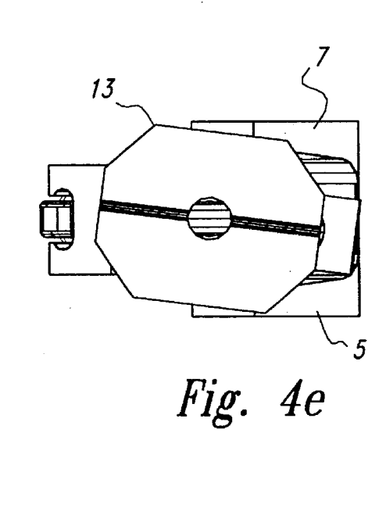
FIGS. 4(e) and (f) are top plan views of the prosthetic ankle joint of FIG. 1 showing how the ankle joint accommodates transverse rotation.
Figure 4F:
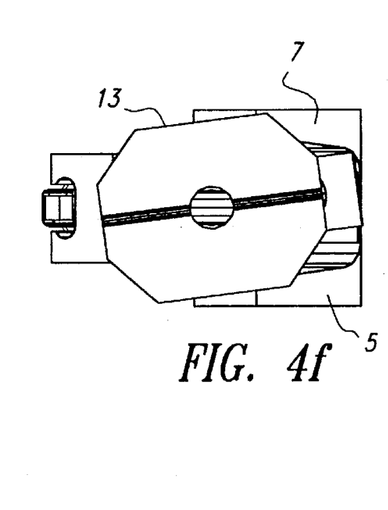

The ankle joint 1 is shown in its assembled condition in FIG. 3. The cushion 5c is interposed between the restraining fin 5 and the base 15, while the other cushion 7c is interposed between the restraining fin 7 and the base 15. The cushions 5c, 7c thus resiliently limit the relative coronal rotation movement between the foot attachment structure 3 and the pylon attachment structure 11 in the coronal plane, as shown in FIGS. 4a and 4b. The cushions 5c, 7c also resiliently limit the relative transverse rotation movement between the foot attachment structure 3 and the pylon attachment structure 11 in the transverse plane as shown in FIGS. 4e and 4f. The cushion 21 is interposed between the base 15 and the support block 9. The cushion 21 thus resiliently limits the relative plantar flexion movement between the foot attachment structure 3 and the pylon attachment structure 11 in the sagital plane as shown in FIG. 4c. The cushion 23 is interposed between the base 15 and a foot attachment plate 70 (FIG. 3). The cushion 23 thus resiliently limits the relative dorsiflexion movement between the attachment structure 3 and the pylon attactment structure 11 in the sagital plane as shown in FIG. 4d. Also, since the pivot axis of the spherical bearing 35 is offset to the rear of where the weight of the user is applied to the pylon attachment plate 13, the weight of the user is supported by both the dorsiflexion cushion 23 and the spherical bearing 35. As a result, the dorsiflexion cushion 23 cushions the downward force exerted by the user during walking in addition to providing resistance to dorsiflexal movement.

As can be seen in FIG. 3, the plantar flexion cushion 21 is a first distance 50 from a longitudinal axis of joint 19. Dorsiflexion cushion 23 is a second distance 60 from the longitudinal axis of joint 19, which is greater than first distance 50. The torque resistance of the dorsiflexion cushion 23 during dorsiflexion is equal to the product of the force exerted by compression of the dorsiflexion cushion 23 and the movement arm 60. Similarly, the torque resistance of the plantar flexion cushion 21 is equal to the product of the force exerted by compression of the plantar flexion cushion 21 and the movement arm 50. Assuming that the spring constants of the cushions 21, 23 are the same, the resistances to dorsiflexion and plantar flexion can be different from each other by simply making the movement arms 50, 60 different from each other.

The angular spring constant K; i.e., the ratio of torque T to angular movement $\theta$ can also be calculated. The torque T is given by the formula:

$$T = Fr \quad (1)$$

where F is the force exerted by the compression of the cushion 21, 23 and r is the movement arm 50, 60, respectively. The force F exerted by the compression of the cushions 21, 23 is given by the formula:

$$F = -Kx \quad (2)$$

where K is the spring constant of the cushions and x is the compression distance of the cushions 21, 23. Substituting the force F from equation (2) into equation (1) yields:

$$T = -Kxr \quad (3)$$

For small angular movements $\theta$, the angle $\theta$ is equal to sin $\theta$. Using this approximation, the cushion compression distance x can be related to the angular movement $\theta$ by the formula:

$$x = r\theta \quad (4)$$

Substituting the cushion compression distance x from formula (4) into formula (3) yields:

$$T = -Kr\theta r = -Kr^2\theta \quad (5)$$

As mentioned above, the angular spring constant K' is equal to the ratio of Torque to angular movement, i.e.:

$$K' = -T/\theta \quad (6)$$

Dividing torque T by angular movement $\theta$ in formula (5) yields:

$$T/\theta = -Kr^2 \quad (7)$$

By setting the ratio of $T/\theta$ in formula (6) to the ratio of $T/\theta$ in formula (7) yields:

$$K' = Kr^2 \quad (8)$$

It is thus seen that the angular spring constant K' is equal to the product of the spring constant K for the cushions 21, 23 and the square of the movement arm 50, 60, respectively.

Thus, the torque resistance of dorsiflexion cushion 23 during dorsiflexion, and of plantar flexion cushion 21 during plantar flexion, will increase as a function of the square of the distance from either cushion to the longitudinal axis of the pin 33. In one version of this embodiment, second distance 60 is greater than first distance 50, thus making resistance during dorsiflexion greater than resistance during plantar flexion. It will be understood, however, that the relative torque resistances during plantar flexion and dorsiflexion can also be varied by using cushions 21, 23 having either different spring constants, different surface areas, different thicknesses, or all three.

Figure 5:
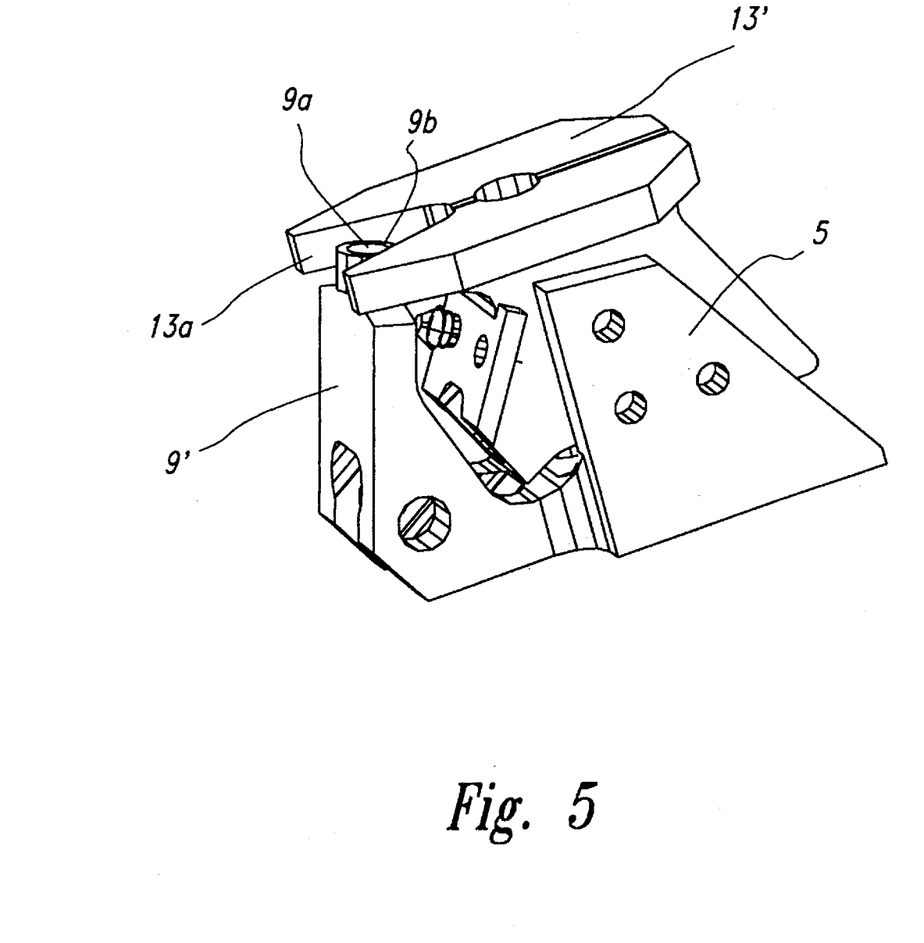
FIG. 5 is an isometric view of another embodiment of the inventive prosthetic ankle joint having coronal rotation limits that vary as a function of plantar flexion and dorsiflexion position.

In another embodiment of the invention illustrated in FIG. 5, the pylon attachment plate 13' has a coronal stabilization notch 13a formed thereon which progressively narrows as it extends into pylon attachment plate 13. In addition, the support block 9' has a coronal stabilization boss 9a projecting from the support block 9 into the coronal stabilization notch 13a. The coronal stabilization boss 9a is surrounded by a bearing 9b.

The coronal stabilization bearing 9b acts in conjunction with the coronal stabilization notch 13a during plantar flexion. As the coronal stabilization boss 9a moves progressively into the notch 13a, coronalflexion is progressively limited. At full plantar flexion, coronal flexion is substantially restricted to stabilize the walking gait of the individual using the prosthetic ankle joint.

Figure 6:
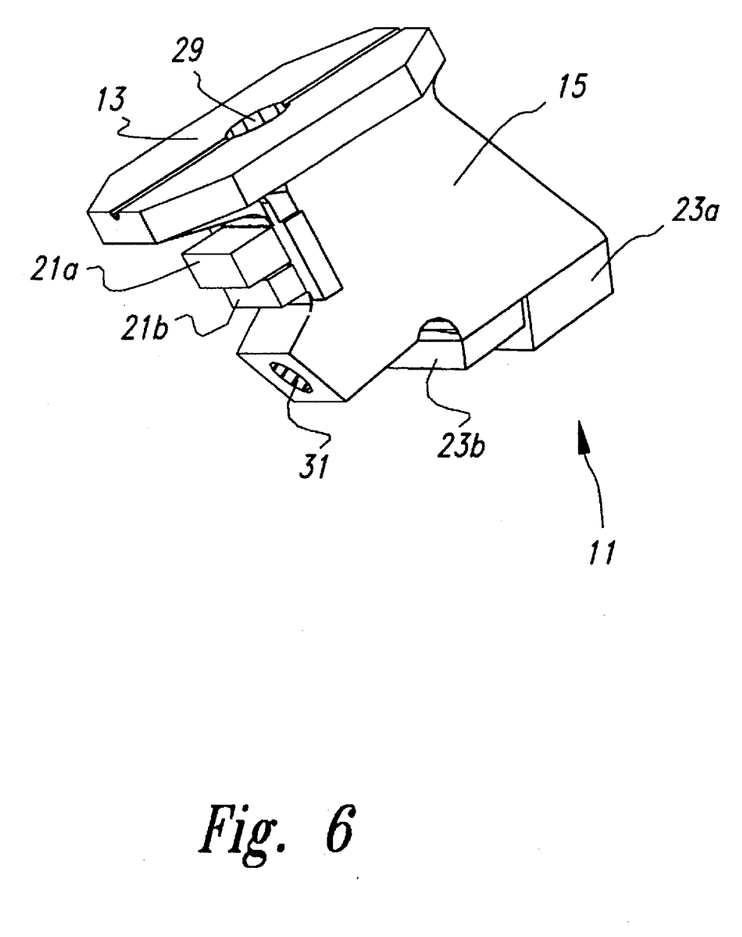
FIG. 6 is an isometric view of still another embodiment of the inventive prosthetic ankle joint having stop cushions of less thickness and greater material stiffness than the primary cushion.

In still another embodiment of the invention illustrated in FIG. 6, two pairs of cushions 21a, 21b, and 23a, 23b are secured to the base 15 to control the flexion characteristics of the ankle joint. These cushions perform the same functions as cushions 21 and 23 discussed above. In addition, the cushion 21b is thinner and has a greater spring constant than the cushion 21a. Similarly, the cushion 23b is thinner and has a greater spring constant than the cushion 23a. As a result, the force exerted by the compression of cushions 21a, 21b and 23a, 23b during dorsiflexion and plantar flexion increases when cushions 21b, 23b begin to compress. This prevents degradation of cushions 21a, 23a from over-compression. For example, if the prosthetic ankle joint is in a state of dorsiflexion where the cushion 23a is compressed but the cushion 23b is not, then the force F exerted by the compression of the cushion 23a is given by the formula:

$$F = -K_{23a}x_{23a} \quad (9)$$

where $K_{23a}$ is the spring constant of the cushion 23a and $x_{23a}$ is the compression distance of the cushion 23a. If the cushion 23b is then also compressed, the force F is given by the formula:

$$F = -K_{23a}x_{23a} + -K_{23b}x_{23b} \quad (10)$$

where $K_{23b}$ is the spring constant of the cushion 23b and $x_{23b}$ is the compression distance of the cushion 23b. Thus, the force F increases as the cushion 23b begins to compress, preventing over-compression of the cushion 23a.

The spring constants of cushions 21b, 23b can be made greater than the spring constants of cushions 21a, 23a by selecting a different material for the cushions with a different modulus of elasticity, by changing the surface area of the cushions, or by changing the thickness of the cushions. This is because the spring constant of the cushion 23b, for example, is given by the formula:

$$K_{23b} = \frac{EA}{l} \quad (11)$$

where E is the modulus of elasticity, A is the surface area, and l is the thickness of the cushion 23b. Thus, for the cushion 23b to have a greater spring constant than the cushion 23a, the modulus of elasticity E or the surface area A of the cushion 23b can be increased, or the thickness the cushion 23b can be decreased.

As discussed above, the thickness l of cushions 21b, 23b is less than the thickness l of cushions 21a, 23a. Preferably, the modulus of elasticity E is also selected to be greater for cushions 21b, 23b than for cushions 21a, 23a. As a result, the spring constants of cushions 21b, 23b are greater than the spring constants for cushions 21a, 23a, allowing cushions 21a, 23a to deform more than cushions 21b, 23b. This has the dual benefits of providing cushions 21a, 23a which can deform to accommodate the majority of plantar flexural and dorsiflexural motion, respectively, while also providing cushions 21b, 23b which carry the majority of the force and keep cushions 21a, 23a from over-compression and resulting degradation. This, in turn, makes the prosthetic ankle joint more reliable.

The ankle 1 can be fabricated from any suitable material, such as aluminum, except that the pins 7b, 5b, 22, and 15b are preferably made of DELRIN™ (ACETAL). The cushions 5c, 7c, cushions 21, 21a, 21b, and cushions 23, 23a, 23b can be made of any resilient material.

Although the present invention has been described in detail, with reference to certain preferred versions, other versions are possible. For example, although the restraining fins 5, 7 are shown as being a part of the foot attachment structure 3, they could instead be a part of the pylon attachment structure 11. In this case, the restraining fins 5, 7 would project downwardly from the foot attachment plate 70 which would now be attached to the pylon, and the pylon attachment plate 13 would be attached to the foot. Therefore, the spirit and scope of the appended claims should not be limited to the description of the preferred versions contained herein.

I claim:

1. A prosthetic ankle joint, comprising:

a first joint structure having a first attachment member attachable to one of either a pylon or a prosthetic foot to receive a force therefrom acting at a first location on the first attachment member, the first joint structure having first and second spaced apart fins each of which substantially lie in a sagital plane;

a second joint structure having a second attachment member attachable to the other of either a pylon or a prosthetic foot to receive a force therefrom acting at a second location on the second attachment member, the second joint structure having a lateral restraining member positioned between the first and second fins;

a spherical bearing interconnecting the first joint structure and the second joint structure so that the first and second joint structures pivot with respect to each other in dorsiflexion, plantar flexion, coronal rotation, and transverse rotation; the pivot point of the spherical bearing being offset from the first and second locations in a direction lying in transverse and sagital planes so that a compressive :force applied between the first and second locations imparts a dorsiflexal or plantar flexal torque about the pivot axis;

a dorsiflexion cushion positioned between the first and second joint structures at a location causing the dorsiflexion cushion to be compressed during dorsiflexal pivotal movement of the ankle joint;

a plantar flexion cushion positioned between the first and second joint structures at a location causing the plantar flexion cushion to be compressed during plantar flexal pivotal movement of the ankle joint; and a lateral cushion positioned between the lateral restraining member and each of the first and second fins so that the lateral cushions are compressed during coronal rotation and transverse rotation pivotal movement of the ankle joint in opposite directions.

2. The prosthetic ankle joint of claim 1 wherein the spherical bearing is connected to the lateral restraining member between the fins of the first joint structure, and wherein the dorsiflexion, plantar flexion, and lateral cushions are positioned adjacent respective surfaces of the lateral restraining member whereby the lateral restraining member serves the functions of both connecting the second joint structure to the spherical bearing and restraining dorsiflexal, plantar flexal, coronal rotational, and transverse rotational pivotal movement of the second joint structure relative to the first joint structure.

3. The prosthetic ankle joint of claim 2 wherein the second attachment member comprises an attachment flange mounted on the lateral restraining member for attaching the second joint structure to a prosthetic pylon.

4. The prosthetic ankle joint of claim 1 wherein the first attachment member comprises a prosthetic foot attachment plate for attaching the first joint structure to a prosthetic foot, and wherein the second attachment member comprises a prosthetic pylon attachment plate for attaching the second joint structure to a prosthetic pylon.

5. The prosthetic ankle joint of claim 1 wherein one of the joint structures includes a plate lying in a transverse plane, the plate having a v-shaped notch extending inwardly from a transverse edge of the plate, and wherein the other of the joint structures includes a restraining member projecting into the notch so that plantar flexal pivotal movement causes the restraining member to move into a narrower portion of the notch whereby the ankle joint is progressively stabilized in the coronal plane as the ankle joint progressively pivots in the plantar flexal direction.

6. The prosthetic ankle joint of claim 1 wherein the spherical bearing includes a spherical bearing member having an aperture extending therethrough and a rod projecting from the spherical bearing member generally perpendicular to the axis of the aperture, wherein the spherical bearing is attached to the first joint structure by an axle attached to the first joint structure and extending through the aperture of the spherical bearing, and wherein the rod of the spherical bearing is attached to the second joint structure.

7. A prosthetic ankle joint, comprising:

a first joint structure attachable to one of either a pylon or a prosthetic foot;

a second joint structure attachable to the other of either a pylon or a prosthetic foot;

a bearing pivotally interconnecting the first joint structure and the second joint structure so that the first and second joint structures can pivot about a pivot axis in dorsiflexion and plantar flexion;

a dorsiflexion cushion positioned between the first and second joint structures at a first location causing the dorsiflexion cushion to be compressed during dorsiflexal pivotal movement of the ankle joint, the first location being spaced from the pivot axis by a first distance; and a plantar flexion cushion positioned between the first and second joint structures at a second location causing the plantar flexion cushion to be compressed during plantar flexal pivotal movement of the ankle joint, the second location being spaced from the pivot axis by a second distance that is different from the first distance so that the torsional spring constant of the prosthetic ankle in dorsiflexion may be different from the torsional spring constant of the prosthetic ankle in plantar flexion using the same material for the dorsiflexion and plantar flexion cushions, the first and second locations both being offset in either a forward or a rearward direction past the pivot point of the bearing so that a compressive force applied between the first and second locations imparts a dorsiflexal torque about the pivot axis whereby the dorsiflexion cushion is compressed by both dorsiflexal pivotal movement between the first and second joint structures and by linear movement between the first and second joint structures toward each other.

8. The prosthetic ankle joint of claim 7 wherein the bearing is a spherical bearing allowing coronal rotational and transverse rotational pivotal movement of the ankle joint as well as dorsiflexal and plantar flexal pivotal movement of the ankle joint.

9. The prosthetic ankle joint of claim 7 wherein the first joint structure includes a prosthetic foot attachment plate for attaching the first joint structure to a prosthetic foot, and wherein the second joint structure includes a prosthetic pylon attachment plate for attaching the second joint structure to a prosthetic pylon.

10. The prosthetic ankle joint of claim 7 wherein one of the joint structures includes a plate lying in a transverse plane, the plate having a v-shaped notch extending inwardly from a transverse edge of the plate, and wherein the other of the joint structures includes a restraining member projecting into the notch so that plantar flexal pivotal movement causes the restraining member to move into a narrower portion of the notch whereby the ankle joint is progressively stabilized in the coronal plane as the ankle joint progressively pivots in the plantar flexal direction.

11. A prosthetic ankle joint comprising:

a first joint structure attachable to one of either a pylon or a prosthetic foot;

a second joint structure attachable to the other of either a pylon or a prosthetic foot, one of the joint structures including a plate lying in a transverse plane, the plate having a v-shaped notch extending inwardly from a transverse edge of the plate, and wherein the other of the joint structures includes a restraining member projecting into the notch so that plantar flexal pivotal movement causes the restraining member to move into a narrower portion of the notch whereby the ankle joint is progressively stabilized in the coronal plane as the ankle joint progressively pivots in the plantar flexal direction;

a bearing pivotally interconnecting the first joint structure and the second joint structure so that the first and second joint structures can pivot about a pivot axis in dorsiflexion and plantar flexion;

a dorsiflexion cushion positioned between the first and second joint structures at a first location causing the dorsiflexion cushion to be compressed during dorsiflexal pivotal movement of the ankle joint, the dorsiflexion cushion having a dorsiflexion cushion thickness in the direction it is compressed;

a plantar flexion cushion positioned between the first and second joint structures at a second location causing the plantar flexion cushion to be compressed during plantar flexal pivotal movement of the ankle joint, the plantar flexion cushion having a plantar flexion cushion thickness in the direction it is compressed; and a stop cushion positioned between the first and second joint structures at a location causing the stop cushion to be compressed during one of either dorsiflexal pivotal movement or plantar flexal pivotal movement and having a stop cushion thickness in the direction the stop cushion is compressed which is less than one of either the dorsiflexion cushion thickness or the plantar flexion cushion thickness, respectively, so that the torsional spring constant of the prosthetic ankle in one of either dorsiflexion or plantar flexion, respectively, is greater when the stop cushion is compressed than when the stop cushion is not compressed.

12. A prosthetic walking system, comprising:

a prosthetic pylon;

a prosthetic foot;

a prosthetic ankle joint connecting the prosthetic pylon to the prosthetic foot, the ankle joint, comprising:

a first joint structure having a first attachment member attachable to one of either the prosthetic pylon or the prosthetic foot to receive a force therefrom acting at a first location on the first attachment member, the first joint structure having first and second spaced apart fins each of which substantially lie in a sagital plane;

a second joint structure having a second attachment member attachable to the other of either the prosthetic pylon or the prosthetic foot to receive a force therefrom acting at a second location on the second attachment member, the second joint structure having a lateral restraining member positioned between the first and second fins;

a spherical bearing interconnecting the first joint structure and the second joint structure so that the first and second joint structures pivot with respect to each other in dorsiflexion, plantar flexion, coronal rotation, and transverse rotation; the pivot point of the spherical bearing being offset in a rearward direction so that a compressive force applied between the first and second locations imparts a dorsiflexal torque about the pivot axis;

a dorsiflexion cushion positioned between the first and second joint structures at a location causing the dorsiflexion cushion to be compressed during dorsiflexal pivotal movement of the ankle joint;

a plantar flexion cushion positioned between the first and second joint structures at a location causing the plantar flexion cushion to be compressed during plantar flexal pivotal movement of the ankle joint; and a lateral cushion positioned between the lateral restraining member and each of the first and second fins so that the lateral cushions are compressed during coronal rotational and transverse rotational pivotal movement of the ankle joint in opposite directions.

13. The prosthetic walking system of claim 12 wherein the spherical bearing is connected to the lateral restraining member between the fins of the first joint structure, and wherein the dorsiflexion, plantar flexion, and lateral cushions are positioned adjacent respective surfaces of the lateral restraining member whereby the lateral restraining member serves the functions of both connecting the second joint structure to the spherical bearing and restraining dorsiflexal, plantar flexal, coronal rotational, and transverse rotational pivotal movement of the second joint structure relative to the first joint structure.

14. The prosthetic walking system of claim 13 wherein the second attachment member comprises an attachment flange mounted on the lateral restraining member for attaching the second joint structure to the prosthetic pylon.

15. The prosthetic walking system of claim 12 wherein the first attachment member comprises a prosthetic foot attachment plate for attaching the first joint structure to the prosthetic foot, and wherein the second attachment member comprises a prosthetic pylon attachment plate for attaching the second joint structure to the prosthetic pylon.

16. The prosthetic walking system of claim 12 wherein one of the joint structures includes a plate lying in a transverse plane, the plate having a v-shaped notch extending forwardly from a rear transverse edge of the plate, and wherein the other of the joint structures includes a restraining member projecting into the notch so that plantar flexal pivotal movement causes the restraining member to move into a narrower portion of the notch whereby the ankle joint is progressively stabilized in the coronal plane as the ankle joint progressively pivots in the plantar flexal direction.

17. A prosthetic walking system, comprising:
a prosthetic pylon;
a prosthetic foot;
a prosthetic ankle joint connecting the prosthetic pylon to the prosthetic foot, the ankle joint, comprising:
a first joint structure attachable to one of either the prosthetic pylon or the prosthetic foot;
a second joint structure attachable to the other of either the pylon or the prosthetic foot;
a bearing interconnecting the first joint structure and the second joint structure so that the first and second joint structures can pivot about a pivot axis in dorsiflexion and plantar flexion;
a dorsiflexion cushion positioned between the first and second joint structures at a first location causing the dorsiflexion cushion to be compressed during dorsiflexal pivotal movement of the ankle joint, the first location being spaced from the pivot axis by a first distance; and
a plantar flexion cushion positioned between the first and second joint structures at a second location causing the plantar flexion cushion to be compressed during plantar flexal pivotal movement of the ankle joint, the second location being spaced from the pivot axis by a second distance that is different from the first distance so that the torsional spring constant of the prosthetic ankle in dorsiflexion may be different from the torsional spring constant of the prosthetic ankle in plantar flexion using the same material for the dorsiflexion and plantar flexion cushions; the pivot point of the spherical bearing being offset in either a forward or a rearward direction past the first and second locations so that a compressive force applied between the first and second locations imparts a dorsiflexal torque about the pivot axis whereby the dorsiflexion cushion is compressed by both dorsiflexal pivotal movement between the first and second joint structures and by linear movement between the first and second joint structures toward each other.

18. The prosthetic walking system of claim 17 wherein the bearing is a spherical bearing allowing coronal rotational and transverse rotational pivotal movement of the ankle joint as well as dorsiflexal and plantar flexal pivotal movement of the ankle joint.

19. The prosthetic walking system of claim 17 wherein the first attachment member comprises a prosthetic foot attachment plate for attaching the first joint structure to the prosthetic foot, and wherein the second attachment member comprises a prosthetic pylon attachment plate for attaching the second joint structure to the prosthetic pylon.

20. The prosthetic walking system of claim 17 wherein one of the joint structures includes a plate lying in a transverse plane, the plate having a v-shaped notch extending forwardly from a rear transverse edge of the plate, and wherein the other of the joint structures includes a restraining member projecting into the notch so that plantar flexal pivotal movement causes the restraining member to move into a narrower portion of the notch whereby the ankle joint is progressively stabilized in the coronal plane as the ankle joint progressively pivots in the plantar flexal direction.

21. A prosthetic walking system comprising:
a prosthetic pylon;
a prosthetic foot;
a prosthetic ankle joint connecting the prosthetic pylon to the prosthetic foot, the ankle joint, comprising:
a first joint structure attachable to one of either a pylon or a prosthetic foot;
a second joint structure attachable to the other of either a pylon or a prosthetic foot;
a dorsiflexion cushion positioned between the first and second joint structures at a first location causing the dorsiflexion cushion to be compressed during dorsiflexal pivotal movement of the ankle joint, the dorsiflexion cushion having a dorsiflexion cushion thickness in the direction it is compressed;
a plantar flexion cushion positioned between the first and second joint structures at a second location causing the plantar flexion cushion to be compressed during plantar flexal pivotal movement of the ankle joint, the plantar flexion cushion having a plantar flexion cushion thickness in the direction it is compressed;
a bearing pivotally interconnecting the first joint structure and the second joint structure so that the first and second joint structures can pivot about a pivot axis in dorsiflexion and plantar flexion, the pivot point of the bearing being offset in a rearward direction so that a compressive force applied between the first and second locations imparts a dorsiflexal torque about the pivot axis whereby the dorsiflexion cushion is compressed by both dorsiflexal pivotal movement between the first and second joint structures and by linear movement between the first and second joint structures toward each other; and
a stop cushion positioned between the first and second joint structures at a location causing the stop cushion to be compressed during one of either dorsiflexal pivotal movement or plantar flexal pivotal movement and having a stop cushion thickness in the direction the stop cushion is compressed which is less than one of either the dorsiflexion cushion thickness or the plantar flexion cushion thickness, respectively, so that the torsional spring constant of the prosthetic ankle in one of either dorsiflexion or plantar flexion, respectively, is greater when the stop cushion is compressed than when the stop cushion is not compressed.

22. A prosthetic walking system comprising:
a prosthetic pylon;
a prosthetic foot;

a prosthetic ankle joint connecting the prosthetic pylon to the prosthetic foot, the ankle joint, comprising:
  a first joint structure attachable to one of either a pylon or a prosthetic foot;
  a second joint structure attachable to the other of either a pylon or a prosthetic foot, one of the joint structures including a plate lying in a transverse plane, the plate having a v-shaped notch extending forwardly from a rear transverse edge of the plate, and wherein the other of the joint structures includes a restraining member projecting into the notch so that plantar flexal pivotal movement causes the restraining member to move into a narrower portion of the notch whereby the ankle joint is progressively stabilized in the coronal plane as the ankle joint progressively pivots in the plantar flexal direction;
  a bearing pivotally interconnecting the first joint structure and the second joint structure so that the first and second joint structures can pivot about a pivot axis in dorsiflexion and plantar flexion;
  a dorsiflexion cushion positioned between the first and second joint structures at a first location causing the dorsiflexion cushion to be compressed during dorsiflexal pivotal movement of the ankle joint, the dorsiflexion cushion having a dorsiflexion cushion thickness in the direction it is compressed;
  a plantar flexion cushion positioned between the first and second joint structures at a second location causing the plantar flexion cushion to be compressed during plantar flexal pivotal movement of the ankle joint, the plantar flexion cushion having a plantar flexion cushion thickness in the direction it is compressed; and
  a stop cushion positioned between the first and second joint structures at a location causing the stop cushion to be compressed during one of either dorsiflexal pivotal movement or plantar flexal pivotal movement and having a stop cushion thickness in the direction the stop cushion is compressed which is less than one of either the dorsiflexion cushion thickness or the plantar flexion cushion thickness, respectively, so that the torsional spring constant of the prosthetic ankle in one of either dorsiflexion or plantar flexion, respectively, is greater when the stop cushion is compressed than when the stop cushion is not compressed.

23. A prosthetic walking system comprising:
a prosthetic pylon;
a prosthetic foot;
a prosthetic ankle joint connecting the prosthetic pylon to the prosthetic foot, the ankle joint, comprising:
  a first joint structure attachable to one of either a pylon or a prosthetic foot;
  a second joint structure attachable to the other of either a pylon or a prosthetic foot;
  a dorsiflexion cushion positioned between the first and second joint structures at a first location causing the dorsiflexion cushion to be compressed during dorsiflexal pivotal movement of the ankle joint, the dorsiflexion cushion having a dorsiflexion cushion thickness in the direction it is compressed;
  a plantar flexion cushion positioned between the first and second joint structures at a second location causing the plantar flexion cushion to be compressed during plantar flexal pivotal movement of the ankle joint, the plantar flexion cushion having a plantar flexion cushion thickness in the direction it is compressed;
  a stop cushion positioned between the first and second joint structures at a location causing the stop cushion to be compressed during one of either dorsiflexal pivotal movement or plantar flexal pivotal movement and having a stop cushion thickness in the direction the stop cushion is compressed which is less than one of either the dorsiflexion cushion thickness or the plantar flexion cushion thickness, respectively, so that the torsional spring constant of the prosthetic ankle in one of either dorsiflexion or plantar flexion, respectively, is greater when the stop cushion is compressed than when the stop cushion is not compressed; and
  a bearing pivotally interconnecting the first joint structure and the second joint structure so that the first and second joint structures can pivot about a pivot axis in dorsiflexion and plantar flexion, the pivot point of the bearing being offset in a rearward direction past the first and second locations so that a compressive force applied between the first and second locations imparts a dorsiflexal torque about the pivot axis where by the dorsiflexion cushion is compressed by both dorsiflexal pivotal movement between the first and second joint structures and by linear movement between the first and second joint structures toward each other.

* * * * *